United States Patent
Skulachev et al.

(10) Patent No.: US 8,349,902 B2
(45) Date of Patent: Jan. 8, 2013

(54) PHARMACEUTICAL COMPOSITIONS USEFUL FOR PREVENTING AND TREATING ONCOLOGICAL DISEASES

(75) Inventors: Vladimir P. Skulachev, Moscow (RU); Maxim V. Skulachev, Moscow (RU)

(73) Assignee: Mitotech SA, Luxembourg (LU)

( * ) Notice: Subject to any disclaimer, the term of this patent is extended or adjusted under 35 U.S.C. 154(b) by 206 days.

(21) Appl. No.: 12/524,961

(22) PCT Filed: Jan. 29, 2007

(86) PCT No.: PCT/RU2007/000044
§ 371 (c)(1), (2), (4) Date: Feb. 16, 2010

(87) PCT Pub. No.: WO2008/094062
PCT Pub. Date: Aug. 7, 2008

(65) Prior Publication Data
US 2010/0144680 A1    Jun. 10, 2010

(51) Int. Cl.
*A01N 31/08* (2006.01)
*A01N 57/26* (2006.01)
*A01N 27/00* (2006.01)
*A61K 31/05* (2006.01)
*A61K 31/685* (2006.01)

(52) U.S. Cl. .................... 514/731; 514/77; 514/764
(58) Field of Classification Search .................... None
See application file for complete search history.

(56) References Cited

U.S. PATENT DOCUMENTS

| | | | |
|---|---|---|---|
| 5,538,974 | A | 7/1996 | Ogawa et al. |
| 6,331,532 | B1 | 12/2001 | Murphy et al. |
| 7,109,189 | B2 | 9/2006 | Murphy et al. |
| 2007/0270381 | A1 | 11/2007 | Murphy et al. |
| 2008/0275005 | A1 | 11/2008 | Murphy et al. |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| RU | 2318500 C2 | 3/2008 |
| WO | 99/26582 A2 | 6/1999 |
| WO | 9926582 | 6/1999 |
| WO | 2004/014927 A1 | 2/2004 |
| WO | 2006/005759 A2 | 1/2006 |
| WO | WO 2006005759 A2 * | 1/2006 |
| WO | 2007/046729 A1 | 4/2007 |
| WO | 2008/048134 A1 | 4/2008 |
| WO | 2009/005386 A1 | 1/2009 |

OTHER PUBLICATIONS

Neidle, Cancer Drug Design and Discovery, Elsevier/Academic Press, 2008, pp. 427-431.*
International Search Report and Written Opinion of the International Searching Authority, PCT/RU2007/000044, Nov. 1, 2007.
Agapova, et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).
Antonenko, et al. (2008) "Mitochondria-Targeted Plastoquinone Derivatives as Tools to Interrupt Execution of the Aging Program. 1. Cationic Plastoquinone Derivatives: Synthesis and In Vitro Studies," Biochem. (Mosc)., 73 (12):1273-1287 (+ 1 fig. page).
Dugina, et al. (2009) "β- and γ-Cyoplasmic Actins Display Distinct Distribution and Functional Diversity," J. Cell Sci., 122(16):2980-2988.
Fernández-Medarde, et al. (2011) "Ras in Cancer and Developmental Diseases," Genes & Canc., 2(3):344-358.
Havens, et al. (2006) "Regulation of Late G1/S Phase Transition and APCCdh1 by Reactive Oxygen Species," Mol. Cell. Biol., 26(12):4701-4711.
Popova, et al., (2010) "Scavenging of Reactive Oxygen Species in Mitochondria Induces Myofibroblast Differentiation," Antiox & Redox. Signal., 13(9):1297-1307.
Pylayeva-Gupta, et al. (2011) "RAS Oncogenes: Weaving a Tumorigenic Web," Nature Reviews/Canc., 11:761-774.
Sundaresan, et al. (1995) "Requirement for Generation of H2O2 for Platelet-Derived Growth Factor Signal Transduction," Science, 270:296-299.
Adlam et al. (2005) "Targeting an antioxidant to mitochondria decreases cardiac ischemia-reperfusion injury," FASEB J., 19:1088-1095.
Anisimov (2007) "Molecular and Physiological Mechanisms of Aging," Antioksidanty, Aug. 27, 2007, [on line] http://imquest.alfaspace.net/BOOK/MFMA/mfma_3_9_2.htm?embedded=yes translated from Russian to English.
Antonenko et al. (2008) "Protective effects of mitochondria-targeted antioxidant SkQ in aqueous and lipid membrane environments," J. Membr. Biol., 222:141-149.
Becker (2004) "New concepts in reactive oxygen species and cardiovascular reperfusion physiology" Cardiovascular Research, 61:461-470.

(Continued)

*Primary Examiner* — James D Anderson
*Assistant Examiner* — Stephanie Springer
(74) *Attorney, Agent, or Firm* — Ann-Louise Kerner; K&L Gates LLP

(57) ABSTRACT

The invention relates to pharmacology, medicine and oncology, in particular, to a class of chemical compounds, the structure of which corresponds to formula (I) and which can be used in pharmaceutical compositions for preventing and treating an extended range of oncological diseases, including, in the form of an anti-tumoral preparation and a preparation which is used for combined therapy of oncological diseases.

6 Claims, 4 Drawing Sheets

OTHER PUBLICATIONS

Berge et al. (1977) "Pharmaceutical Salts," J. Pharma. Sci., 66(1):1-19.

Blaikie et al. (2006) "Targeting Dinitrophenol to Mitochondria: Limitations to the Development of a Self-limiting Mitochondrial Protonophore," Biosci. Rep, 26:231-243.

Brand et al. (1992) "The mechanism of the increase in mitochondrial proton permeability induced by thyroid hormones," Eur. J. Biochem. 206:775-781.

Doughan et al. (2007) "Original Research Communication: Mitochondrial Redox Cycling of Mitoquinone Leads to superoxide Production and Cellular Apoptosis," Antioxid. & Redox Signal., 9(11):1825-1836.

Emiko et al. (2005) "Manganese Superoxide Dismutase protects against oxidation-induced apoptosis in mouse retinal pigment epithelium: implications for age-related macular degeneration," Invest. Ophthalmol. Vis. Sci., 46(9):3426-3434.

Green et al. (2004) "Prevention of Mitochondrial Oxidative Damage as a Therapeutic Strategy in Diabetes," Diabetes, 53(1):S110-S118.

Hansford et al. (1997) "Dependence of H2O2 formation by rat heart mitochondria on substrate availability and donor age," J. Bioenerg. Biomem. 29(1):89-95.

Holloszy (1998) "Longevity of exercising male rats: effect of an antioxidant supplemented diet," Mechanisms of Ageing and Development, 100:211-219.

King et al. (2004) "Mitochondria-derived reactive oxygen species mediate blue light-induced death of retinal pigment epithelial cells," Photochem. and Photobiol, 79(5):470-475.

Kirschner et al. (1994) "Role of iron and oxygen-derived free radicals in ischemia-reperfusion injury" J. Am. Coll. Surg., 179:103-117.

Li et al. (2000) "Skeletal muscle respiratory uncoupling prevents diet-induced obesity and insulin resistance in mice," Nat. Med. 6(10):1115-1120.

Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.

Longo et al. (2005) "Programmed and altruistic ageing," Nature Reviews Genetics, 6:866-872.

Lou et al. (2007) "Mitochondrial Uncouplers With an Extraordinary Dynamic Range," Biochem. J., 407:129-140.

Mecocci et al. (2000) "Plasma antioxidants and longevity: a study on healthy centenarians," Free Radical Biology and Medicine, 28(8):1243-1248.

Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.

Orr et al. (2003) "Effects of overexpression of copper-zinc and manganese superoxide dismutases, catalase, and thioredoxin reductase genes on longevity in Drosophila melanogaster," J. Biol. Chem., 278(29):26418-26422.

Papp et al. (1999) "Glutathione status in retinopathy of prematurity," Free Radic. Biol. & Med., 27(7-8):738-743.

Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.

Petrosillo et al. (2006) "Protective effect of melatonin against mitochondrial dysfunction associated with cardiac ischemia-reperfusion: role of cardiolipin," FASEB J., 20:269-276.

Popova et al. (2006) "MitoQ induced miofibroblast differentiation of human fibroblasts," Biochimica et Biophysica Acta, S:433-434.

Pozniakovsky et al. (2005) "Role of mitochondria in the pheromone- and amiodarone-induced programmed death of yeast," J. Cell Biol., 168(2):257-69.

Reddy (2006) "Mitochondrial oxidative damage in aging and Alzheimer's disease: implications for mitochondrially targeted antioxidant therapeutics," J. Biomedicine and Biotech., Art.ID 31372:1-13.

Reliene et al. (2007) "Antioxidants suppress lymphoma and increase longevity in the atm-deficient mice," J. Nutrition, 37:229S-232S.

Riess et al. (2004) "Reduced reactive O2 species formation and preserved mitochondrial NADH and [Ca2+] levels during short-term 17° C. ischemia in intact hearts," Cardiovascular Research, 61:580-590.

Skulachev (2007) "A Biochemical Approach to the Problem of Aging: 'Megaproject' on Membrane-Penetrating Ions. The First Results and Prospects," Biochem. (Moscow), 72(12):1385-1396.

Sheu et al. (2006) "Targeting antioxidants to mitochondria: a new therapeutic direction," Biochimica et Biophysica Acta, 1762:256-265.

Sidorova et al. (2004) "Transcriptional activation of cytochrome P450 1A1 with alpha-tocopherol," Bull Exp. Bio. Med., 138(3):233-236.

Skulachev (2005) "Critical Review: How to Clean the Dirtiest Place in the Cell: Cationic Antioxidants as Intramitochondrial ROS Scavengers," IUBMB Life, 57(4/5):305-310.

Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.

Starkov et al. (1997) "6-ketocholestanol is a recoupler for mitochondria, chromatophores and cytochrome oxidase proteoliposomes," Biochim. Biophys. Acta. 1318:159-172.

Tompkins et al.(2006) "Mitochondrial dysfunction in cardiac ischemia-reperfusion injury: ROS from complex I, without inhibition," Biochim Biophys Acta 1762:223-231.

Yildirim et al. (2005) "Role of oxidative stress enzymes in open-angle glaucoma," Eye, 19:580-583.

Zweier et al. (1987) "Direct measurement of free radical generation following reperfusion of ischemic myocardium," PNAS USA, 84:1404-1407.

International Search Report dated Dec. 20, 2007 and International Preliminary Report on Patentability dated Nov. 10, 2009, PCT/RU2007/000171 (16 pages).

International Search Report and Written Opinion of the International Searching Authority, PCT/RU2007/000355, Mar. 27, 2008, 10 pages.

PCT International Preliminary Report on Patentability for International Application No. PCT/RU2007/000043, issued Aug. 4, 2009, 7 pages.

PCT International Search Report for PCT Application No. PCT/RU2007/000043, mailed Nov. 1, 2007, 2 pages.

PCT International Search Report and Written Opinion of the International Searching Authority for PCT Application No. PCT/RU2006/000546, mailed Jul. 5, 2007, 14 pages.

International Search Report, PCT/RU2008/000706, Aug. 13, 2009 (3 pages).

International Search Report and Written Opinion of the International Searching Authority, PCT/RU2009/000295, Feb. 25, 2010, 7 pages.

International Search Report and Written Opinion, PCT/RU2009/000621, dated Aug. 12, 2010 (12 pages).

International Search Report and Written Opinion, PCT/RU2006/000394, dated Nov. 2, 2006 (6 pages).

International Search Report and Written Opinion, PCT/RU2006/000547, dated Jul. 5, 2007 (7 pages).

\* cited by examiner control

Ras-transformed cells

Cells reincubated with SkQ1

Ras-transformed cells reincubated with SkQ1

PHARMACEUTICAL COMPOSITIONS USEFUL FOR PREVENTING AND TREATING ONCOLOGICAL DISEASES

BACKGROUND OF THE INVENTION

Although there are lot of different home- and foreign-made anti-tumoral preparations in clinical practice, their efficiency is in most cases insufficient and range of diseases sensitive to chemotherapy is limited. Due to this, question of new more active preparations development and search of compositions, effective in tumor with primary and gained resistance, remains of current interest.

WO2006005759 reports on mitochondrially targeted antioxidants application for ontological diseases therapy. This patent states that treatment of mice with tumor xenografts (tumors of epithelial cancers) with mitochondrially targeted antioxidant MitoQ [current compound is excluded from applicant's application] leads to tumor size reduction, increased necrosis and decreased vascularization of the tumor xenografts.

However no experimental data proving relevance of these statements was shown; examples of pharmaceutical compositions, which could be used for the purpose, (including active compound (MitoQ) concentrations), administration methods and doses are not represented in the application as well. Furthermore, no quantitative data on anti-tumoral effect of the used compound were represented, meanwhile on the current stage of anti-cancer technology a development quantitative assessment of preparation therapeutical effect is a key factor which determines a possibility of preparation application as an anti-tumoral drug. In addition to this, MitoQ composition possesses pro-oxidant influence, that may indeed lead to consequences, stated by the authors. In such a way application WO2006005759 is more about mitochondrially targeted pro-oxidants anti-tumoral effect, and thus does not solve the problem of ontological diseases treatment with mitochondrially targeted antioxidants.

Potential described ability of compositions to possess an anti-tumoral effect is also mentioned in author's application, registered as RU 2005132217 and dated Oct. 19, 2005. However represented experimental data provides only potential ability of application of mitochondrially targeted bioactive compositions for cancer preventing or therapy.

DESCRIPTION OF INVENTION

One of the aspects of the present invention is a pharmaceutical composition for preventing and/or treatment of oncological diseases, consisting of targeting part, linker group and antioxidant. In general, such a compound can be described by the following structure (I):

$$A \underset{n}{\overbrace{L}} B$$

wherein A is effector moiety—antioxidant and/or reduced form thereof wherein m is an integer from 1 to 3; each Y is independently selected from the group consisting of: lower alkyl, lower alkoxy; or two adjacent Y groups, together with carbon atoms to which they are attached, form a following structure:

and/or reduced form thereof wherein R1 and R2 may be the same or different and are each independently lower alkyl or lower alkoxy;

L—linker group, comprising:
  a) straight or branched hydrocarbon chain which can be optionally substituted by one or more substituents and optionally contains one or more double or triple bonds;
  b) natural isoprene chain;
  n is integer from 1 to 20;
  B—targeting group, comprising
  a) Skulachev-ion Sk:
    $Sk^+Z^-$
  where Sk—lipophilic cation, Z—pharmacologically acceptable anion;
  b) charged hydrophobic peptide containing 1-20 amino acid residues;

with proviso that in compound of structure (I) A is not ubiquinone (e.g. 2-methyl-4,5-dimethoxy-3,6-dioxo-1,4-cyclohexadienyl) or tocopherol or mimetic of superoxide dismutase or ebselen; while L—divalent decyl or divalent pentyl or divalent propyl radical; and while B is triphenylphosphonium cation or it's solvates, isomers and prodrugs thereof.

Further aspect of the present invention is a pharmaceutical composition for preventing and/or treatment of oncological diseases, one comprising a composition of Structure (II) wherein A—plastoquinone of structure:

wherein Y—methyl, m=2;
L—linker group, comprising:
  a) straight or branched hydrocarbon chain optionally substituted with one or more substituents and optionally containing one or more double or triple bonds;
  b) natural isoprene chain;
  n is integer from 1 to 20;
  B—comprising:
  a) Skulachev-ion Sk:
    $Sk^+Z^-$
  where Sk is a lipophilic cation, Z is a pharmacologically acceptable anion;
  b) charged hydrophobic peptide containing 1-20 amino acid residues;

with proviso that in compound of structure (I) A is neither ubiquinone (e.g. 2-methyl-4,5-dimethoxy-3,6-dioxo-1,4-cyclohexadienyl) nor tocopherol or mimetic of superoxide dismutase or ebselen; with L—neither divalent decyl nor divalent pentyl or divalent propyl radical; and with B is triphenylphosphonium cation or it's solvates, isomers or prodrugs thereof.

Further aspect of the invention is a pharmaceutical composition for preventing and treatment of oncological diseases, one comprising a composition of Structure (I)—SkQ1:

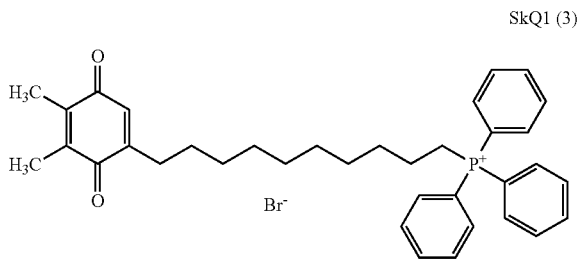 [SMILES: CC1=C(C)C(=O)C(CCCCCCCCCC[P+](c2ccccc2)(c2ccccc2)c2ccccc2)=CC1=O ; [Br-]]

SkQ1 (3)

Further aspect of the invention is a pharmaceutical composition for preventing and treatment of oncological diseases that comprises therapeutically or prophylactically justified amount of a compound of Structure (I) and at least one pharmacologically acceptable solvent or carrier. A pharmacologically acceptable solvent or carrier may present filler, a diluent (solvent) or their mixture. "Therapeutically justified" amount of a compound is amount of a compound of Structure (I) that causes desired biological or medical response in a patient treated by a doctor or a veterinarian. "Prophylactically justified" amount of a compound is amount of a compound of Structure (I) that prevents or suppresses the disease, or relieves progress of the disease in a patient suffering from a medical state that is tried to be prevented, suppressed or relieved by a doctor or a veterinarian.

In one of the aspects of the present invention a human is a patient.

Different oncological diseases includes without limitations: malignant growths of lip, mouth cavity, malignant growths of digestive apparatus, malignant growths of respiratory apparatus and thoracic organs, malignant growths of bones and articular cartilages, melanoma and other dermal malignant growth, malignant growths of mesothelial and soft tissues, malignant growth of breast, malignant growth of female reproductive organs, malignant growths of male reproductive organs, malignant growths of urinary tracts, malignant growths of eye, cerebrum and other parts of CNS, malignant growths of thyroid body and other internal secretion glands, malignant growth of roughly specified, postprimary or not specified localizations, malignant growths of lymphoid, hemogenic and their congenial tissues.

Malignant growths of lip, mouth cavity and pharynx include but not limited by lip malignant growths, tongue malignant growths, tongue base malignant growths, malignant growths of non-specified parts of tongue, back of tongue malignant growth, tongue flank malignant growths, tongue lower surface malignant growths, lingual tonsil malignant growths, malignant growth of gingival, mouth floor malignant growths, malignant growths of mouth floor flank, malignant growths of mouth floor forepart, palate malignant growths, kion malignant growths and malignant growths of other non-specified mouth portions, buccal mucosa malignant growths, buccal cavity malignant growths, malignant growths of retromolar area, parotid gland malignant growths, submandibular gland malignant growths, sublingual gland malignant growths, amygdale malignant growths, amygdaloid fossa malignant growths, oropharynx malignant growths, malignant growths of epiglottis fossa, malignant growth of epiglottis forehead, malignant growth of epiglottis flank wall, malignant growths of epiglottis back wall, malignant growths of branchial fissure, rhinopharynx malignant growth, malignant growths of pyriform sinus, malignant growths of pharynx lower part, malignant growth of pharynx lower part back wall.

Malignant growth of digestive apparatus includes but not limited by: malignant growths of esophagus, gaster malignant growths, small intestine malignant growths, dodecadactylon malignant growths, empty intestine malignant growths, twisted intestine malignant growths, malignant growths of Meckel's diverticulum, small intestine malignant growths of non-specified localization, blind intestine malignant growths, vermicular appendix malignant growths, ascending colon malignant growth, malignant growth of segmented intestine hepatic arc, transverse colon malignant growths, malignant growths of segmented intestine lienal arc, descending colon malignant growths, sigmoid colon malignant growths, malignant growths of rectosigmoid junction, straight intestine malignant growths, malignant growths of fundament and anal canal, cloacogenic area malignant growths, malignant growths of liver and intrahepatic biliary tracts, hepatocellular carcinoma, intrahepatic biliary tract cancer, hepatoblastoma, liver angiosarcoma and other liver sarcomas, malignant growths of gall bladder, extrahepatic bile duct malignant growths, malignant growths of major duodenal papilla, pancreatic gland malignant growths, malignant growths of the head of pancreas, malignant growths of the body of pancreas, malignant growths of the tail of pancreas, pancreatic duct malignant growths, pancreatic islet malignant growths, malignant growths of lien.

Malignant growths of respiratory apparatus and thoracic organs includes but not limited by: malignant growths of nasal cavity and middle ear cavity, malignant growths of paranasal sinuses, gorge malignant growths, trachea malignant growths, bronchial and lung malignant growths, thymus malignant growths, heart malignant growths, malignant growths of pleura and inter-pleural space, upper air passages' malignant growths of non-specified localization.

Dermal malignant growths includes but not limited by: malignant melanoma of skin, malignant melanoma of lip, malignant melanoma of eyelid, comprising palpebral commissure, malignant melanoma of ear and external auditory canal, malignant melanoma of head and neck pilous areas, body malignant melanoma, malignant melanoma of upper limb, comprising shoulder joint area, malignant melanoma of lower limb, comprising hip joint and other dermal malignant growths.

Malignant growths of mesothelial and soft tissues include but not limited by: mesothelioma, mesothelioma of pleura, mesothelioma of peritoneum, mesothelioma of pericardium, peripheral nerves, involuntary nervous system and Kaposi's sarcoma, malignant growths of peritoneum and retroperitoneal space, malignant growths of other types of connective and soft tissues.

Malignant growths of female reproductive organs include but not limited by: malignant growths of trema, vaginal malignant growths, malignant growth of uterine cervix, malignant growths of uterine body, ovarian malignant growths, placenta malignant growths.

Malignant growths of male reproductive organs include but not limited by: malignant growths of phallus, malignant growths of prostate gland, testis malignant growth.

Malignant growths of urinary tracts include but not limited by: malignant growths of kidney, malignant growths of pelvis of kidney, ureter malignant growth, malignant growth of urinary bladder, malignant growth of urethra, malignant growth of Littre's glands.

Malignant growths of eye, cerebrum and other parts of CNS include but not limited by: malignant growths of eye and adventive apparatus, malignant growths of brain tunic, malignant growths of cerebrum, malignant growths of spine, cranial nerves and other segments of CNS, malignant growths of CNS.

Malignant growths of thyroid body and other internal secretion glands include but not limited by: malignant growth of thyroid body, malignant growths of adrenal body, malignant growths of other internal secretion glands and relative formations, malignant growths of parathyroid gland, hypophysis malignant growths, malignant growths of craniopharyngeal duct, malignant growths of epiphysis, malignant growths of intercarotid body, malignant growths of aortic body and other paraganglia.

Malignant growths of lymphoid, hemogenic and their congenial tissues include but not limited by: Hodgkin's disease [megakaryoblastoma], Hodgkin's disease—lymphoid superiority (lymphocyte-rich type), Hodgkin's disease—nodular sclerosys, Hodgkin's disease mixed-cellularity subtype, Hodgkin's disease—lymphocyte-depleted type, other types of Hodgkin's disease, Hodgkin's disease—unspecified type, follicular non-Hodgkin's lymphoma, small cleaved cell lymphoma, follicular, mixed, small cleaved cell lymphoma and large cell, large cell follicular lymphoma, other types of follicular non-Hodgkin's lymphoma, follicular lymphoma non-specified form, diffuse non-Hodgkin's lymphoma, small cell diffuse lymphoma, diffuse small cleaved cell lymphoma, diffuse mixed small and large cell lymphoma, diffuse large cell lymphoma—reticulosarcoma, diffuse immunoblastic lymphoma, diffuse lymphoblastic lymphoma, diffuse non-differentiated lymphoma, Burkitt's lymphoma, diffuse non-specified non-Hodgkin's lymphoma, peripheral and dermal T lymphomas, granulosarcoid, Sezary syndrome, zone T lymphoma, Lennert's lymphoma, peripheral T lymphoma, other non-specified T lymphomas, lymphosarcoma, non-specified T lymphoma, malignant immunoproliferative diseases, Waldenström macroglobulinemia, alpha heavy-chain disease, gamma heavy-chain disease, immunoproliferative diseases of small intestine, other immunoproloferative diseases, multiple myeloma and malignant cell plasma growths, plasma cell leukemia, plasmacytoma, extramedullary plasmacytoma, lymphocytic leukemia, acute lymphoblastic leukemia, inveterate lymphoblastic leukemia, prolymphocytic leukemia, hairy-cell leukemia (leukemic reticuloendotheliosis), adult T cell leukemia, myeloblastosis, acute myeloblastosis, inveterate myeloblastosis, subacute myeloblastosis, myeloid sarcoma (green cancer—chloroma, granulocytic sarcome), acute progranulocytic leukemia, acute myelomonocytic leukemia, monocytic leukemia, acute monocytic leukemia, inveterate monocytic leukemia, subacute monocytic leukemia, acute erythremia and erythroleukemia, inveterate erythremia, acute megakaryoblastic leukemia, mast cell leukemia, acute panmyeloleukemia, acute myelofibrosis, Letterer-Seve disease (non-lipidic reticuloendotheliosis, reticulosis), malignant histiocytosis, malignant mast cell tumor, pure histiocytic lymphoma.

Compositions of Structure (I) can be used for efficient preventing and therapy of all types of cancer along with negative consequences and side effects of cancer therapy regardless to its causes.

Application of pharmaceutical compositions related to the invention can be both systemic and local. Methods of administration comprise enteral, such as oral, sublingual and rectal; local, such as percutaneous, intradermal and oculodermal, and parenteral. Acceptable parenteral administration methods comprise injections, such as endovenous, intramusculary, hypodermic, intraperitoneal, intra-arterial etc injections, and non-injectional methods, such as intravaginal and nasal. Preferably compounds and pharmaceutical compositions, related to present invention, should be administrated parenteral and per oral. In particular, order can be done in form of intravenous injections or tablets, granules, capsules or any in different pressed compressed form.

When a compound of structure (I) is administered as a pharmaceutical composition, the compound of structure (I) should be mixed according to formula with a suitable amount of pharmacologically acceptable solvent or carrier so that to have the appropriate form for administration to a patient. The term "solvent" relates to diluent, auxiliary medicinal substance, filler or carrier which is mixed with the compound of structure (I) for administration to a patient. Liquors like water, and oils including petrolic, animal, vegetative and synthetic such as peanut oil, soybean oil, mineral oil and other similar oils can be used as said pharmacological carriers. Normal saline solution, acacia pitch, gelatin, starch, talc, keratin, colloid silver, urea etc can serve as said pharmacological solvents. Said composition can also include auxiliary substances, stabilizers, thickeners, lubricant and coloring agents.

The compounds and compositions of the present invention can be administered in the form of capsules, tablets, pills, pillets, granules, syrups, elixirs, solutions, suspensions, unctures, creams, sprays, emulsions, suppositories, retarded release substances, or in any other form suitable for administration to a patient. A further aspect of present invention is application of compounds of Structure (I) and pharmaceutical compositions in form of solutions for per oral or parenteral administration.

Therapeutically justified amount of a compound of Structure (I) required for treatment of a specific disease or symptom, depends on the nature of disease or symptom and a method of administration and should be determined at consultation with a physician in charge. Acceptable doses for per oral administration are from 0.025 for 120000 microgram per kilogram of weight of patients body, more preferably around 25 mkg/kg and the most preferable dose is around 50 mkg/kg of weight of patient's body. Acceptable doses for endovenous administrations are from 0.1 to 10000 mkg/kg of weight of patients body, more preferably around 25 mkg/kg and the most preferable dose is around 125 mkg/kg of weight of patient's body.

Examples of acceptable pharmaceutical compositions for per oral administration:

Pharmaceutical Compositions—1—Gelatinous Capsules.

| Ingredient | Ammount (mg/capsule) |
|---|---|
| Composition of structure I | 0.0015-1000 |
| Amylum | 0-650 |
| Amylum powder | 0-650 |
| Liquid silicone | 0-15 |

Pharmaceutical Composition—2—Tablets

| Ingredient | Ammount (mg/capsule) |
|---|---|
| Composition of structure I | 0.0015-1000 |
| Microcrystalline cellulose | 200-650 |

-continued

| Ingredient | Ammount (mg/capsule) |
| --- | --- |
| Silicon dioxide powder | 10-650 |
| Stearic acid | 5-15 |

Pharmaceutical Composition—3—Tablets

| Ingredient | Ammount (mg/capsule) |
| --- | --- |
| Composition of structure I | 0.0015-1000 |
| Amylum | 45 |
| Microcrystalline cellulose | 35 |
| polyvinylpyrrolidone (10% aqueous solution) | 4 |
| Carbossimetilcellulose sodium salt | 4.5 |
| Talc | 1 |
| Magnesium stearate | 0.5 |

Pharmaceutical Compulsion—4—Suspensions

| Ingredient | Ammount (mg/5 ml) |
| --- | --- |
| Composition of structure I | 0.0015-1000 |
| Sirup | 1.25 |
| Benzoic acid solution | 0.10 |
| Carbossimetilcellulose sodium salt | 50 |
| Flavor additive | if necessary |
| Food grade dye | if necessary |
| Water (distilled) | Up to 5 ml |

Example of Acceptable Pharmaceutical Composition for Administration in Form of Spray:

| Ingredient | Ammount (percent by weight) |
| --- | --- |
| Composition of structure I | 0.0025 |
| Etanol | 25.75 |
| Difluorochloromethane | 70 |

Example of Acceptable Pharmaceutical Composition for Administration in Form of Suppositories:

| Ingredient | Ammount (mg/suppository) |
| --- | --- |
| Composition of structure I | 1 |
| Saturated fatty acid glyceride | 2000 |

Example of Acceptable Pharmaceutical Composition for Administration in Form of Solution for Application Per Os (pH 6.5):

| Ingredient | Ammount |
| --- | --- |
| Composition of structure I | 5 mg |
| Isotonic solution | 1000 ml |

DETAILED DESCRIPTION OF THE INVENTION

Experimental Examples

Experimental Example 1

Effect of SkQ1 on Ras-Transformed Fibroblast Cells Morphology and Adherence

Experiment was carried out using cells, transformed with genetic construct, expressing oncogene RAS, and thus modeling conditions of cells underwent cancerous transformation. (see model description in Levina E M, Domnina L V, Rovensky Y A, Vasiliev J M., (1996), Exp. Cell. Res., November 25, pp 159-65). Mouse Ras-transformed fibroblast cells had strongly expressed changed morphology (see FIG. 1.), one close to morphology of metastasizing cancerous cells (decrease in surface square, cell elongation). Morphological analysis demonstrated cell surface square mean values to be significantly decreased in comparison to control (see FIG. 2.). Cytoskeleton elements and focal contact proteins—vinculin and paxillin—content was drastically decreased in these cells. Cells were poorly adherent and spread-eagled what led to monolayer structure disorder. All these features are peculiar for metastasizing cancerous cells with comparatively increased mobility.

Figure 1:
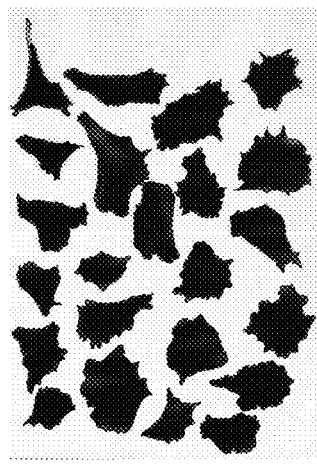
FIG. 1 shows effect of SkQ1 on morphology of normal and Ras-transformed mouse fibroblasts.
Figure 1:
Figure 1:
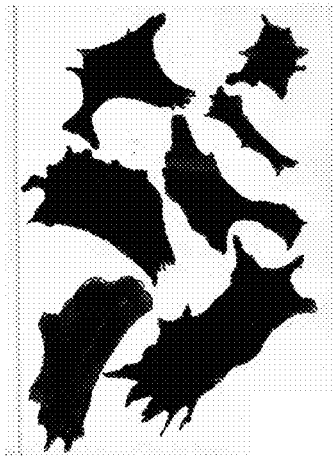
Figure 1:
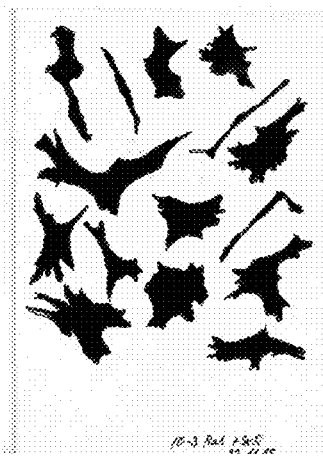
Figure 2:
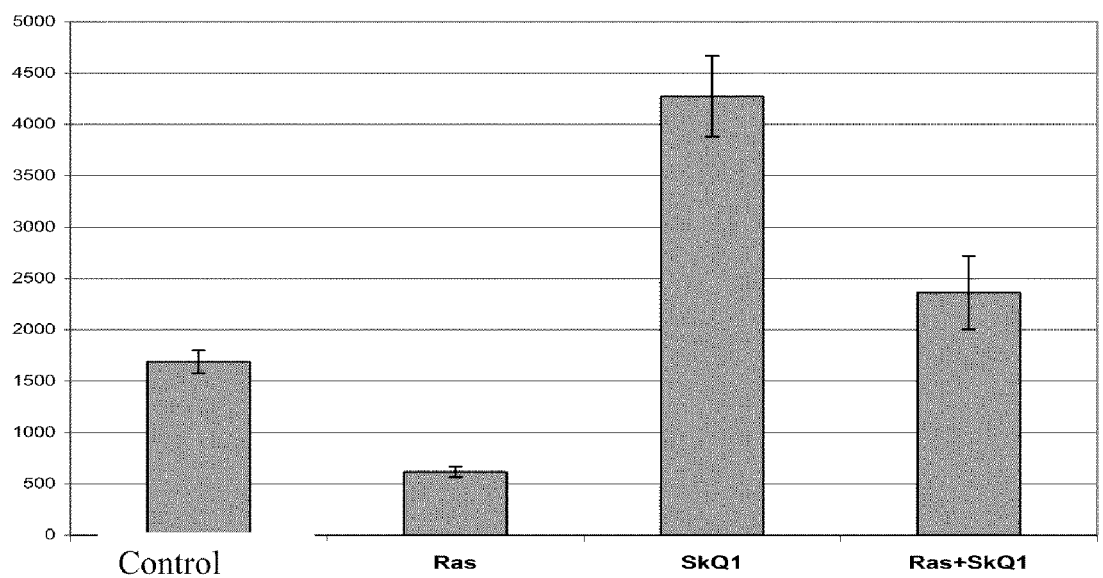
FIG. 2 shows effect of SkQ1 on surface square of normal and Ras-transformed mouse fibroblasts.

However incubation with SkQ1 led to significant changes in cells morphology (see FIG. 1.). Mean cell surface square value increased manifold (see FIG. 2.) Morphological changes correlated with actinic fibrils increase in content, focal contact reinforcement and cell better adherence to the surface. Ras-transformed fibroblasts treated with SkQ1 formed monolayers similar to those of normal fibroblasts.

Obtained results demonstrate that in model system treatment of metastasizing cancerous cells with SkQ1 led to normalization of its condition.

Experimental Example 2

Study of SkQ1 Anti-Tumoral Activity on A-431 Human Skin Cancer Heteroxenografts Transplanted to HIV Mice Experiment was carried out taking into account Russian the Federation Ministry of Health Care and international recommendations, published in the following sources: Larionov L F, Chemotherapy of malignant tumor, Moscow., 1962; Treshchalina E M and co-authors, Methodical recommendations on study of anti-tumoral activity of pharmacological substances in the book: "Guidance on experimental (preclinical) study of new pharmacological substances" edited by corresponding member of Russian Academy of Medical Sciences prof. Habriev R U, 2005; Experimental evaluation of antitumor drugs in the USA and USSR and clinical correlations, NCI Monograph 55, 1980; Survey and antitumor toxicity test systems, EORTC Screening and Pharmacology group, 1989; Anticancer drug development guide: Preclinical screening, clinical trials, and approval, Edt. Teicher B. A., 1997.

Studied Preparation

Before introduction SkQ1 was diluted with sterile physiological saline up to two use rates 0.5 μM and 5.0 μM. Preparation was introduced intraperitoneally in single doses 5.0 nM/kg and 50.0 nM/kg in the volume 0.2 ml/mouse.

Tumor Cell Culture

Experiment was carried out using A-431 cell line [1], lodged in Russian collection of collection of cell cultures and possessed the following features:

Origin: human, epithelial carcinoma J. Natl. Cancer Inst. 1973. 51: 14171423.
Morphology: epithelial.
Cultivation method: monolayer
Cultivation conditions: 10% bovine embryonal serum DMEM culture.
Procedure of seeding: cell removal using 0.25% trypsin, 0.02% versene (3:7), ratio of seeding 1:3 1:6, optimal density $2.04.0 \times 10^4$ cell per $sm^2$ cryopreservation media, 10% DMSO, $1.0 \times 10^6$ cells/ml per ampoule
Viability after cryopreservation: 83% (trypan blue staining on zero passage)
Contamination control: no bacteria, fungi or microplasma detected
Genetic identity control: karyological, enzymatic (LDH, G6PDH) analysis.
Caryology: 2n–46, chromosome variability limit 5777, chromosome modal number 6871
Tumorigenicity: tumorigenic in HIV mice and in mice treated with antithymocyte serum.
Other features: large number of receptors to epidermal growth factor.
Application area: growth factors study, cell biology.
Collection: ATCC CRL 1555; ECACC 85090402; INC RAS.

A-431 cells were grown on RPMI-1640 medium that contained 10% calf serum and 1 mM of glutamine. Cells were transferred to a flask in ratio 1:2 or 1:3 from full monolayer. Medium was changed every 2-3 days. Cultivated cell suspension then was used to engraft HIV mice.

Mammals and Implanted Tumors

Experiment was performed using HIV female mice Balb/c nude at the age 8-9.5 weeks. All mice were raised in GU RONC. Mice were managed in specialized virus-free chamber with sterile aeration, fed with sterile briquette food and water under normalized temperature condition and moisture.

Cells of A-431 cell line were hypodermically implanted only once in number $1.7-1 \times 10^6$ per mouse in 0.2 ml of nutrition medium RPMI-1640.

Anti-Tumoral Effect Estimation

Anti-tumoral effect estimation was carried out using common rate T/C (Treatment/Control), evaluated as a ratio of average tumor volumes in treated and control groups given in percents. Rate was taken evaluated using the following formula T/C %=(Vo/Vk)/(Vk)×100%, where Vo and Vk—mean volumes of tumor in treated and control groups thereof. Thus in control group T/C=100%. Mean volume was evaluated using the following formula Vm (mm³)=a×b×c. T/C≤42% was taken as a minimal efficiency criterion [Anticancer Drug Development Guide, edt. by B. A. Teicher, Humana Press, Totowa, N.J., 1997, p. 101-125]. For tumor growth speed analysis (standarcy value) a ratio of mean tumor value in following estimations to a first one was teken.

Evaluation started after appearance of palpable tumor (9 day after implantation). After that a multiple tumor volume evaluations were performed until $20^{th}$ day after transplantation. In such a way in treated groups first evaluation was performed in process of treatment, and three next evaluations—during 6 days after end of the treatment. Tumor evaluations were stopped on $21^{st}$-$24^{th}$ day after first mouse died in three experiments.

Tolerance to the treatment was estimated according to time of death corresponded to treatment with each preparation.

Histological Research

Mice were mortified by ether anaesthesia overdose, an autopsy was performed, tumors were then extracted and a histological and immunohistochemical assays were carried out.

Tumors were fixed in 10% formaldehyde, set into paraffin wax. Histological assays were carried out on tumor histological sections, stained with hematoxylin and eosin. Study of number of micro-vessels was performed with standard immunological method using antibodies to CD34 antigen. Presence of vessel mimicry was, estimated by tumor section staining with Schiff's reagent.

Obtained Results:

Study of anti-tumoral activity was performed in three experiments.

Experiment 1

At the "zero" day all mice were hypodermically engrafted with cells of A-431 cell line in concentration $1.7 \times 10^6$ per mouse in 0.2 ml of nutrition medium RPMI-1640. After implantation all mice very divided in groups 7 mice in each.

Two of the studying groups intraperitoneally received SkQ1 preparation every day from $1^{st}$ to $14^{th}$ day after tumor implantation.

Group 1 (control): average weight of the mouse 20.3[19.6÷21.0] g, intraperitoneally received 0.2 ml of physiological saline from $1^{st}$ to $14^{th}$ day after tumor implantation.

Group 2: average weight of the mouse 19.9[19.2÷20.6] g, from $1^{st}$ to $14^{th}$ day after tumor implantation mice were intraperitoneally injected with SkQ1 preparation in single dose 5.0 nM/kg, sum dose 70.0 nM/kg.

Group 3: average weight of the mouse 19.8[19.1÷20.5] g, from $1^{st}$ to $14^{th}$ day after tumor implantation mice were intraperitoneally injected with SkQ1 preparation in single dose 50.0 nM/kg, total dose 700.0 nM/kg.

Results:

Group 1 (control). Mean tumor volume values (Vm) comprised 458[318÷598] mm³, 1295[959÷1631] mm³, 1996[1319÷2673] mm³ and 2564[2064÷3064] mm³ on $9^{th}$, $14^{th}$, $17^{th}$ and $20^{th}$ day after transplantation thereof. Ratio of mean volumes of growing tumors comprised correspondingly 2.83-4.36-5.6 times. Growths factors demonstrate tumor development speed to be normal for mice hypodermic tumors in 20 day period.

First mouse died on $22^{nd}$ day of tumor. Autopsy revealed no visual sings of pathological changes in mouse organs. Rest of mice were mortified on $23^{rd}$ day after transplantations, again autopsy demonstrated no pathological changes in mice organs.

Group 2 (SkQ1 preparation in single dose 5.0 nM/kg). Mean tumor volume values (Vm) comprised 289[87÷1491] mm³, 95 [515÷1395] mm³, 1349[903÷1793] mm³ and 1863 [919÷2807] mm³ on $9^{th}$, $14^{th}$, $17^{th}$ and $20^{th}$ day after transplantation thereof. Anti-tumoral effect at these stages comprised T/C=63, 74, 67, 73% thereof. No statistical differences with control group were found (p>0.05). Treatment tolerance stated satisfactory. Mice started to die on 7-8 days after end of the treatment—two mice died on $21^{st}$-$22^{nd}$ days after transplantation; autopsy revealed no visual sings of pathological changes in mice organs. Rest of mice were mortified on $23^{rd}$ day after transplantations, again autopsy demonstrated no pathological changes in mice organs.

Group 3 (SkQ1 preparation in single dose 50.0 nM/kg). Mean tumor volume values (Vm) comprised 730[430÷1030] mm³, 2078 [1328÷2828] mm³, 2678 [1667÷3689] mm³ and 3557[2042÷5072] mm³ on $9^{th}$, $14^{th}$, $17^{th}$ and $20^{th}$ day after transplantation thereof. Anti-tumoral effect at these stages comprised T/C=159, 160, 134, 146% thereof. Treatment tolerance stated satisfactory. All mice were mortified on $23^{rd}$ day after transplantations, autopsy demonstrated no pathological changes in mice organs.

Due to represented data the following may be concluded:

In group 3, received treatment with SkQ1 preparation in single dose 50.0 nM/kg, T/C comprised 134-160% what gives evidence of potential stimulation of tumor growth.

In group 2 after 8 injections of SkQ1 preparation in single dose 5.0 nM/kg tumor growth was inhibited and T/C comprised 63%. Total dose up to moment of the effect registration comprised 40.0 nM/kg. Further injections led to no additional effect but no growth acceleration was registered either. A suggestion that the preparation can be efficient when given 8 times in single dose 5.0 nM/kg (total dose 40.0 nM/kg) was made.

Experiment 2

At the "zero" day all mice were hypodermically engrafted with cells of A-431 cell line in concentration $1.0 \times 10^6$ per mouse in 0.2 ml of nutrition medium RPMI. After implantation all mice very divided in 2 groups 10 mice in each.

Experimental group intraperitoneally received SkQ1 preparation every day from $1^{st}$ to $8^{th}$ day after tumor implantation:

Group 1 (control): average weight of the mouse 20.8[19.8÷21.8] g, intraperitoneally received 0.2 ml of physiological saline from $1^{st}$ to $8^{th}$ day after tumor implantation.

Group 2: average weight of the mouse 20.1[19.6÷20.6] g, from $1^{st}$ to $8^{th}$ day after tumor implantation mice were intraperitoneally injected with SkQ1 preparation in single dose 5.0 nM/kg, sum dose 40.0 nM/kg.

Results:

Group 1 (control). Mean tumor volume values (Vm) comprised 155[117÷193] mm³, 1008[828÷1188] mm³, 1641[1152÷2130] mm³ and 2936[2261÷3611] mm³ on $8^{th}$, $14^{th}$, $17^{th}$ and $24^{th}$ day after transplantation thereof. Ratio of mean volumes of growing tumors comprised correspondingly 6.5-10.5-18.9 times. Growths factors demonstrate a comparatively high speed of tumor development in this experiment.

First mouse died on $24^{th}$ day of tumor. Autopsy revealed no visual sings of pathological changes in mouse organs. Rest of mice were mortified on $24^{th}$ day after transplantations, again autopsy demonstrated no pathological changes in mice organs.

Group 2 (SkQ1 preparation in single dose 5.0 nM/kg). Mean tumor volume values (Vm) comprised 95[55÷135] mm³, 724[441÷1007] mm³, 1582[1007÷2157] mm³ and 2953[1730÷4176] mm³ on $8^{th}$, $14^{th}$, $17^{th}$ and $24^{th}$ day after transplantation thereof. Anti-tumoral effect at these stages comprised T/C=61, 72, 96, 101% thereof. First mouse died on the 16 yh day after treatment end and in the same day with first death in control group. Autopsy of died and mortified mice revealed no visual singes of pathological changes in mice organs.

Obtained results demonstrated, that 8-day treatment with 5.0 nM/kg single dose of SkQ1 preparation of HIV mice with human skin cancer A-431 heteroxenografts led to replicable inhibition of tumor growth (T/C=61%).

Experiment 3

At the "zero" day all mice were hypodermically engrafted with cells of A-431 cell line in concentration $1.0 \times 10^6$ per mouse in 0.2 ml of nutrition medium RPMI. After implantation all mice very divided in 2 groups 9 mice in each.

Studied group intraperitoneally received SkQ1 preparation every day from $1^{st}$ to $14^{th}$ day after tumor implantation:

Group 1 (control): average weight of the mouse 18.8[18.3÷19.3] g, intraperitoneally received 0.2 ml of physiological saline from $1^{st}$ to $8^{th}$ day after tumor implantation.

Group 2: average weight of the mouse 18.8[18.3÷19.3] g, from $1^{st}$ to $14^{th}$ day after tumor implantation mice were intraperitoneally injected with SkQ1 preparation in single dose 5.0 nM/kg, sum dose 70.0 nM/kg.

Results:

Group 1 (control). Mean tumor volume values (Vm) comprised 94[9÷179] mm³ and 567[274÷1107] mm³ on $14^{th}$ and $21^{st}$ days after transplantation thereof. Growths factors demonstrate a comparatively low speed of tumor development in this experiment.

First mouse died on $21^{st}$ day of tumor. Autopsy revealed no visual sings of pathological changes in mouse organs. Rest of mice were mortified on $23^{th}$ day after transplantations, again autopsy demonstrated no pathological changes in mice organs.

Group 2 (SkQ1 preparation in single dose 5.0 nM/kg). Mean tumor volume values (Vm) comprised 39[6÷72] mm³ and 256[94÷418] mm³ on $14^{th}$ and $21^{st}$ day after transplantation thereof. Immediately after end of the treatment a significant anti-tumoral effect was registered T/C comprised T/C=41%.

Tolerance to the treatment stated satisfactory. First mouse died on the 7th day after treatment end. Autopsy of died and mortified mice revealed no visual singes of pathological changes in mice organs.

Obtained results demonstrated, that immediately after end of 14-day treatment with 5.0 nM/kg single dose of SkQ1 preparation of HIV mice with human skin cancer A-431 heteroxenografts preparation possessed minimal anti-tumoral effect T/C=42%.

Histological Study

Histological and immunohistochemical analyses of tumor sections were performed on material obtained in experiment 1.

Histological assay revealed tumor xenografts possess typical structure of non-differentiated tumor of epithermal type. Comparison of control samples with those of group 2 demonstrated that SkQ1 preparation in single dose 5 nM/kg causes partial tumor differentiation: signs of keratinization appear in tumor tissue.

Number of micro-vessels was counted in so-called hot spots—tumor areas with maximal vascularization. According to our data, number of micro-vessels in tumors ($23^{rd}$ day, $9^{th}$ day after end of the treatment) didn't statistically differ in all three groups. However, micro-vessels in group 2 were mentioned to be of smaller diameter than in control group.

Sample staining with PAS reagent revealed tumors in control group to possess sings of vasculagenic mimicry, while no such singes were mentioned in tumors in group 2.

Conclusion

Experimental study on SkQ1 treatment effect on HIV mice with human skin cancer A-431 hypodermic xenografts revealed that long-termed injection of SkQ1 in single doses 5.0 nM/kg didn't cause tumor growth acceleration, and in some cases led to growth 50% inhibition.

Injection of SkQ1 in single dose 5.0 nM/kg causes partial differentiation of A-431 tumor tissue, decreases sings of vasculagenic mimicry, though does not affect total number of micro-vessels.

Experimental Example 3

Study on SkQ1 Preparation Anti-Tumoral Effect on Mice Tumors (Hypodermic Introduction of Ehrlich's Carcinoma)

Experimental Scheme.

Experiment was performed according to recommendations listed in description of experimental example 2.

Injection of preparation started after 48 hours after transplantation and proceeded during 5, 10, 15 and 30 days. For tumor treatment efficiency estimation tumor volumes were evaluated many times after end of short courses or once after end of 30-day course. Efficiency was judged according to standard tumor growth suppression factor (TGS) in comparison to control group that didn't receive a treatment and results were calculated in percents. Obtained results were then statistically calculated, using confidence intervals of mean values of compared values, difference stated reliable if $p<0.05$.

As was demonstrated, SkQ1 preparation in single dose 0.5 nM/kg possessed short-time inhibition effect on tumors of mice with hypodermic Ehrlich's carcinoma immediately after end of 5-day course (TGS=40-50%). Ten-fold dose increase or increase of injection number didn't lead to prolongation of said effect. Thus 5-day treatment course should be considered as minimal efficient course.

Cells in amount 1 million were hypodermically implanted to thymus-deprived mice.

Mice in each group were divided to 4 sub-groups 10 mice in each:

group received water to drink group received water with SkQ1—0.01 nmol of preparation per mouse per day (0.5 nM/kg/day)

group received water with SkQ1—0.1 nmol of preparation per mouse per day (5 nM/kg/day)

group received water with SkQ1—1 nmol of preparation per mouse per day (50 nM/kg/day)

Size of tumors was evaluated every 3 days. After 4 weeks mice were mortified, tumors were fixed for histological assay.

Figure 3:
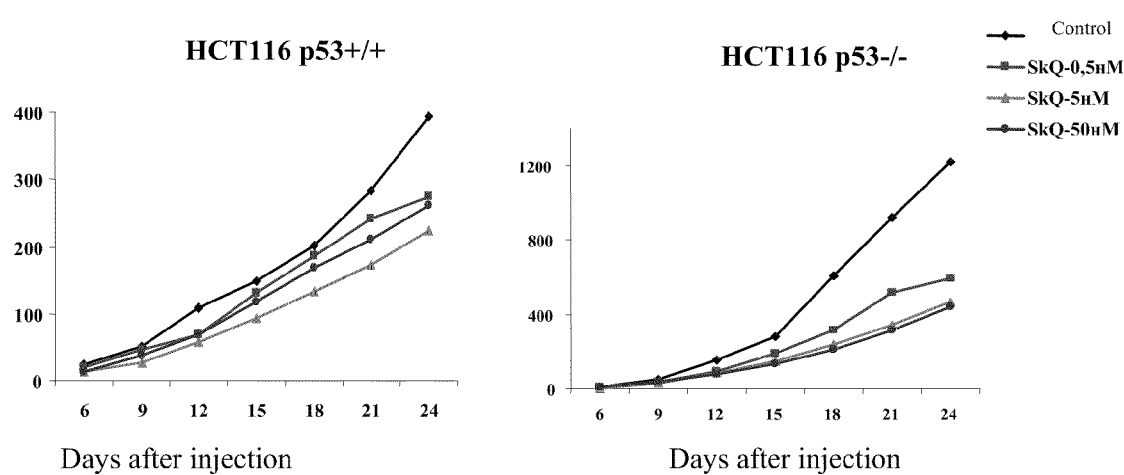
FIG. 3 shows effect of SkQ1 on growth of tumors from HCT116-p53 wt and HCT116-p53−/− cell lines.
Figure 4:
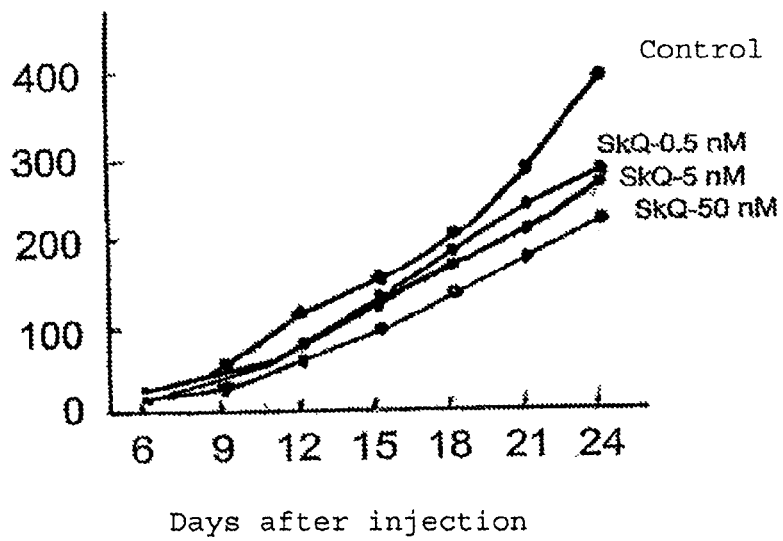
FIG. 4 shows effect of SkQ1 on growth of HCT116 xenografts.
Figure 4:
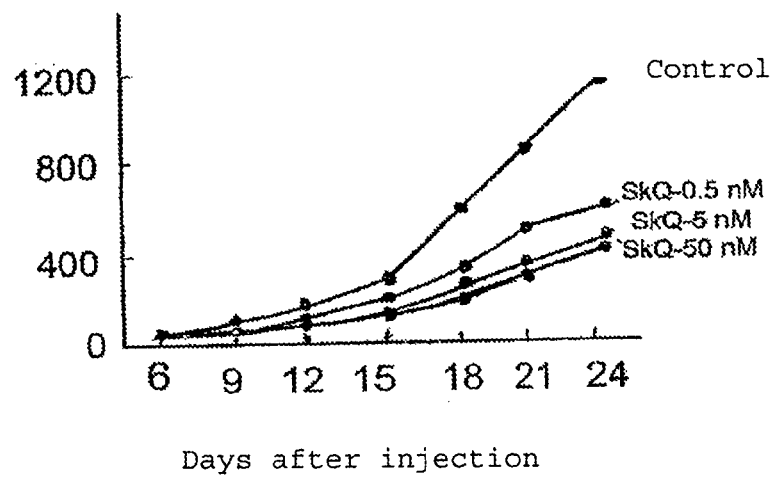

According to obtained data, addition of SkQ1 preparation in drinking water led to tumor growth suppression in comparison to control group, one that received pure water; changes in growth speed were significantly higher in tumors with inactivated p53 than in tumors with p53 of wild type (see FIG. 3). The most efficient concentration appears to be 0.1 nmol per mouse per day (5 nM/kg/day).

Due to received data addition of SkQ1 has stronger effect on tumor with inactivated p53 compared to tumors with wild-type p53.

TABLE 1

Results of experiments with implanted Ehrlich's carcinoma.

| Number of mice | Single dose | Day of therapy | Way of introduction | Day after transplantation | | |
|---|---|---|---|---|---|---|
| | | | | 7 | 14 | 21 |
| Control, ph. s. 15 days | | | | | | |
| N = 10 | Ph. s. 0.2 ml | — | ip | 416 [328 ÷ 504] | 716 [543 ÷ 889] | 1188 [460 ÷ 1916] |
| SkQ1 preparation, 5-day course | | | | | | |
| N = 10 | 0.5 nM/kg | 2-7 | ip | 251 [134 ÷ 368] | 547 [319 ÷ 775] | 1000 [462 ÷ 1538] |
| | TGS %* | | | 40 | 23 | 16 |
| SkQ1 preparation, 10-day course | | | | | | |
| N = 10 | 0.5 nM/kg | 2-13 | ip | 228 [120 ÷ 336] | 474 [210 ÷ 738] | 853 [299 ÷ 1407] |
| | TGS % | | | 45 | 34 | 28 |
| SkQ1 preparation, 15-day course | | | | | | |
| N = 10 | 0.5 nM/kg | 2-16 | ip | 259 [150 ÷ 368] | 459 [319 ÷ 599] | 838 [945 ÷ 1131] |
| | TGS % | | | 38 | 36 | 29 |

Experimental Example 4

Study of SkQ1 Preparation's Anti-Tumoral Effect on Human Large Intestine Carcinoma Two human large intestine carcinoma cell sub-lines that differ by p53 status—wild type cells (HCT116 p53+/+)) and cells with inactivated p53 (HCT116 p53−/−)) (cell line cultivation see in Bunz, F., Dutriaux, A., Lengauer, C., Waldman, T., Zhou, S., Brown, J. P., Sedivy, J. M., Kinzler, K. W., and Vogelstein, B. (1998) Science, 282, pp 1497-1500, see model description in Sablina A A, Chumakov P M, Kopnin B P. (2003), J. Biol. Chem., 278, pp. 27362-27371).

Experimental Example 5

Development of Joined Therapy with SkQ1 and Doxorubicin Chemotherapy

For development of oncological diseases joint therapy that combines SkQ1 and chemotherapy, a study on SkQ1 influence on single doxorubicin injection efficiency was performed (one of mechanisms of the preparation is activation of oxidative processes in normal and cancerous cells). SkQ1 was introduced before, simultaneously or after introduction of doxorubicin in maximum dose 500 nM/kg (in order to block oxidative mechanism of doxorubicin influence).

Table 2 demonstrates results of study on efficiency of joint introduction of SkQ1 introduced in dose 500 nM/kg in 0.2 ml/mouse during 5 days in form of alcohol solution and doxorubicin introduced in all variants intraperitoneally in a dose 7 mg/kg on $7^{th}$ day after transplantation. Schemes of doxorubicin application allow its introduction before, after and during the course of SkQ1.

SkQ1 monotherapy was demonstrated to 33% suppress growth of tumor immediately after end of course. Anti-tumoral effect of doxorubicin, applied on $7^{th}$ day—when tumor was already fully developed, was less expressed. TGS comprised 26% and 36% on $10^{th}$ and $14^{th}$ day thereof.

Of all studied schemes of joint application of SkQ1 and doxorubicin, the most efficient appears to be a scheme with 5-day-long course of SkQ1 "before" introduction of doxorubicin. Maximal TGS was registered on $10^{th}$ day (61%) and stayed up to $21^{st}$ day. An important thing is that effect of SkQ1 on $7^{th}$ day was the same in groups received SkQ1 as monotherapy and with aftergoing introduction of doxorubicin—TGS comprises 33 and 39% thereof. Different schemes of joint application of SkQ1 and doxorubicin proved to be ineffective. In these variants therapeutic effect didn't exceed effect of doxorubicin and were lower than one of SkQ1.

Due to this, the most efficient scheme appears to be one that comprises introduction of doxorubicin after SkQ1 course (5-day-long). Addition of SkQ1 to drinking water appeared to increased HIV mice immunity to infectious diseases, what was registered though estimation of mouse life-span when managed in chamber without sterile aeration.

SkQ1 efficiency demonstrated to depend on p53 status in the tumor. Addition of SkQ1 preparation (maximal effect—5 nM of SkQ1) to drinking water inhibits growth of tumors with inactivated SkQ1 stronger than in tumors of p53 wild type.

Application of SkQ1 (500 nM, 5-day-long course) before introduction of doxorubicin appear to be most efficient (maximal TGS was registered on $10^{th}$ day (61%) and remains the same until $21^{st}$ day). Different schemes of joint therapy—application of doxorubicin before or during SkQ1 course—appear to be ineffective.

TABLE 2

Effect of SkQ1 (alcohol solution) combined with doxorubicin on growth of lung Lewis's carcinoma.

| Group | Dose mg/kg, regime and way of introduction | TGS %, by tumor volume Days | | | | |
|---|---|---|---|---|---|---|
| | | 7 | 10 | 14 | 17 | 21 |
| Control[1] | 0.2 ml/mouse alcohol solution per.os. × 10 | 199 ± 66 | 1006 ± 182 | 3034 ± 354 | 5596 ± 1100 | 10575 ± 3243 |
| SkQ | 500 nmol, 0.2 ml/ mouse per.os. × 5 (2-6 days) | 33 | 42 | 48 | 28 | 30 |
| DOX | DOX (7 mg/kg × $17^{th}$ day ip | —[2] | 26 | 38 | 35 | 30 |
| SkQ + DOX | 500 nmol, 0.2 ml/ mouse per.os. × 5 (2-6 days) + DOX (7 mg/kg × $17^{th}$ day ip | 39[2] | 61 | 58 | 51 | 50 |
| SkQ + DOX + SkQ | 500 nmol, 0.2 ml/ mouse per.os. × 5 (5, 6, 7, 8, 9) + DOX (7 mg/kg × $17^{th}$ day ip | —[2] | 23 | 37 | 23 | 29 |
| DOX + SkQ1 | DOX (7 mg/kg × $17^{th}$ day ip + 500 nmol, 0.2 ml/mouse per.os. × 5 (8, 9, 10, 11, 12) | —[2] | 18 | 24 | 28 | 6 |

[1]As a control
— volumes of tumors in control group are given in mm3
[2]day of doxorubicin introduction

The invention claimed is:

1. A method of treating a cancer in a mammal selected from the group consisting of lung carcinoma, large intestine carcinoma, cervical carcinoma, skin carcinoma, colon cancer, Lewis carcinoma, fibrosarcoma, osteosarcoma, rhabdomyosarcoma, epithelial carcinoma, neuroblastoma, and lymphoma, comprising administering to the mammal a therapeutically effective amount of a pharmaceutical composition comprising the compound SkQ1 having the structure:

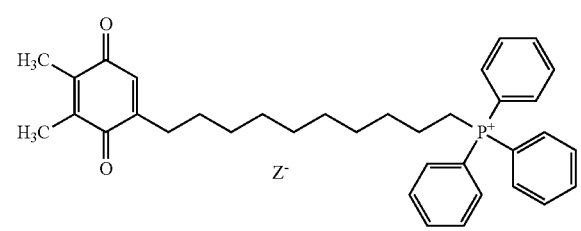

or a solvate or isomer thereof to said mammal, where $Z^-$ is a pharmaceutically acceptable anion.

2. The method of claim 1, wherein the pharmaceutical composition is administered with another anti-cancer therapeutic.

3. The method of claim 1, wherein the pharmaceutical composition is a solution and is orally administered.

4. The method of claim 1, wherein the pharmaceutical composition is a solution and is parenterally administered.

5. The method of claim 1, wherein the pharmaceutical composition is an ointment, bandage, or film and is transdermally administered.

6. The method of claim 1, wherein the cancer is a Ras-related metastatic cancer.

* * * * *